ically a
United States Patent [19]
Christie et al.

[11] Patent Number: 4,932,966
[45] Date of Patent: Jun. 12, 1990

[54] ACCOMMODATING INTRAOCULAR LENS

[75] Inventors: Bruce A. Christie, Newport-Richey; Brian M. McMaster, Safety Harbor, both of Fla.; J. Warren Blaker, Bronx, N.Y.

[73] Assignee: Storz Instrument Company, St. Louis, Mo.

[21] Appl. No.: 232,600

[22] Filed: Aug. 15, 1988

[51] Int. Cl.$^5$ .............................................. A61F 2/16
[52] U.S. Cl. ........................................................ 623/6
[58] Field of Search ............................................ 623/6

[56] References Cited

U.S. PATENT DOCUMENTS

| | | |
|---|---|---|
| 1,518,405 | 12/1924 | Glancy . |
| 2,086,493 | 7/1937 | Ellingwood . |
| 2,227,461 | 1/1941 | Morin et al. . |
| 2,244,565 | 6/1941 | Nast . |
| 2,253,132 | 8/1941 | Malson . |
| 2,631,585 | 3/1953 | Siebrandt . |
| 2,698,483 | 1/1955 | Berkowitz . |
| 2,743,726 | 5/1956 | Grieshaber . |
| 2,878,721 | 3/1959 | Kanolt . |
| 2,985,556 | 5/1961 | Rowland . |
| 3,034,403 | 5/1962 | Neefe ................................ 623/6 X |
| 3,040,746 | 6/1962 | Chester . |
| 3,209,753 | 10/1965 | Hawkins et al. . |
| 3,270,099 | 8/1966 | Camp . |
| 3,339,997 | 9/1967 | Wesley . |
| 3,454,332 | 7/1969 | Siegel . |
| 3,458,870 | 8/1969 | Stone, Jr. . |
| 3,555,126 | 1/1971 | Gitson . |
| 3,589,369 | 6/1971 | Alksnis . |
| 3,614,217 | 10/1971 | Bronstein . |
| 3,711,870 | 1/1973 | Deitrick .............................. 623/6 |
| 3,726,587 | 4/1973 | Kendall . |
| 3,794,414 | 2/1974 | Wesley . |
| 3,913,148 | 10/1975 | Potthast ............................. 623/6 |
| 3,950,082 | 4/1976 | Volk . |
| 4,010,496 | 3/1977 | Neefe ................................. 623/6 |
| 4,024,870 | 5/1977 | Sandel . |
| 4,102,567 | 7/1978 | Cuffe et al. . |
| 4,118,853 | 10/1978 | Mignen . |
| 4,122,556 | 10/1978 | Poler ................................. 623/6 |
| 4,143,427 | 3/1979 | Anis .................................. 623/6 |
| 4,159,546 | 7/1979 | Shearing ............................. 623/6 |
| 4,170,043 | 10/1979 | Knight et al. ....................... 623/6 |
| 4,172,297 | 10/1979 | Schlegel ............................. 623/6 |
| 4,174,156 | 11/1979 | Glorieux . |
| 4,190,049 | 2/1980 | Hager et al. . |
| 4,198,980 | 4/1980 | Clark . |
| 4,206,518 | 6/1980 | Jardon et al. ....................... 623/6 |
| 4,214,585 | 7/1980 | Bailey, Jr. . |
| 4,253,199 | 3/1981 | Banko ................................ 623/6 |
| 4,254,509 | 3/1981 | Tennant .............................. 623/6 |
| 4,315,673 | 2/1982 | Guilino et al. . |
| 4,316,293 | 2/1982 | Bayers ............................... 623/6 |
| 4,325,375 | 4/1982 | Nevyas . |
| 4,338,005 | 7/1982 | Cohen . |

(List continued on next page.)

FOREIGN PATENT DOCUMENTS

| | | |
|---|---|---|
| 1103399 | 11/1955 | France ............................... 623/6 |
| 939016 | 10/1963 | United Kingdom . |
| 1547200 | 6/1979 | United Kingdom . |

OTHER PUBLICATIONS

Lens Styles from Cilco–Mar. 1984 (6 pages).
Catalogue No. 469–"The Rayner Choyce Mark VIII Anterior Chamber Implant", Kayner & Keeler Limited (3 pages).
The Surgical Armamentarium, Instruments and Equipment, p. 878–1980.
J. Warren Blaker, "Modern Lens Design for Today & Tomorrow", Break-Out Session: Amer. Society of Cataract & Refractive Surgery–Seminar Apr. 9, 1986.

Primary Examiner—Ronald L. Frinks

[57] ABSTRACT

An accommodating intraocular lens apparatus preferably includes a lens member having a relatively flexible portion and a relatively rigid portion, with a fluid-filled chamber therebetween. The preferred intraocular lens also includes a hydraulic or other fluid accommodation provision for changing the shape or position of the flexible lens by changing the fluid pressure in the fluid-filled chamber in response to muscle movement of the eye.

28 Claims, 4 Drawing Sheets

ACCOMMODATING INTRAOCULAR LENS

BACKGROUND AND SUMMARY OF THE INVENTION

The invention relates generally to intraocular lenses for the human eye and, more particularly, to intraocular lenses that change in refractive power (i.e. "accommodate") in response to eye muscle movement to focus on objects at different distances as viewed from the viewer.

Figure 1:
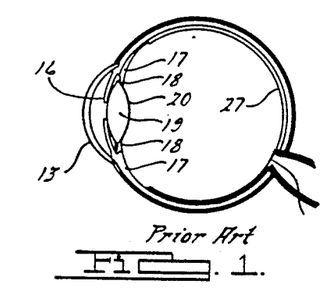
FIG. 1 diagrammatically illustrates a human eye in cross-section.
Figures 2A, 2B:
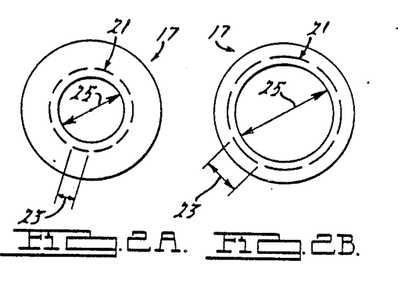
FIGS. 2A and 2B diagrammatically illustrate dilation of the ciliary body of the eye.

FIGS. 1 through 4 illustrate the accommodation function of a normal, natural human eye, with FIG. 1 showing a human eye in cross-section. The eye structure includes a cornea 13, an iris 16, a ciliary body 17, suspensory ligaments or zonules of zinn 18, a crystalline lens 19 surrounded by a capsular bag 20, and a retina 27. The ciliary body 17 includes muscle tissue, which controls the focal length of the lens 19. When individual circumferential muscle fibers 21 of the ciliary body 17 relax (i.e., when the dimensions 23 increase), the aperture diameter 25 within the ciliary body 17 increases, as shown in FIGS. 2A and 2B.

Figure 3A:
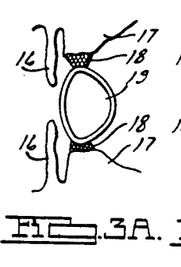
FIGS. 3A and 3B diagrammatically illustrate how the dilation shown in FIG. 2B stretches the crystalline lens and changes its focal length.
Figure 3B:
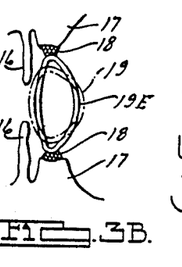

As shown in FIGS. 3A and 3B, this increase in aperture diameter puts tension on the zonules 18, which in turn stretch the crystalline lens 19, causing the lens 19 to assume elongated shape 19E. the elongated lens 19E has a refractive power suitable for focusing distant objects upon the retina 27. When it is necessary to focus nearby objects, the muscle fibers 21 of ciliary body 17 contract, decreasing the aperture diameter 25 shown in FIG. 2A. In response to this contraction, the inherent elasticity of the lens 19 causes it to contract to the unstretched shaped shown in FIG. 3A. This ability of the human optical system to change the shape of the lens 19 (and thus the refractive power) in order to focus on either distant or nearby objects is called "accommodation".

The lens 19 of the human eye can, however, suffer disease, such as a cataract, in which case surgical removal of the lens 19 may be necessary. After removal, the natural lens 19 can be replaced by an artificial lens 32 shown in FIG. 4, which is termed an intraocular lens (IOL). One type of IOL 32 is shown in FIGS. 5A and 5B. The lens 32 is supported by haptics 36, which rest generally at points 37 in FIG. 4 after implantation in the eye.

Figure 4:
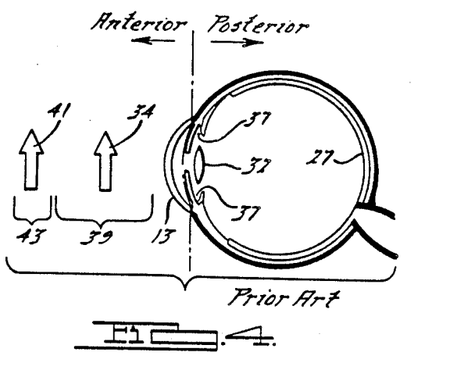
FIG. 4 illustrates an intraocular lens that can be used to replace the natural lens 19 in FIG. 1.
Figure 5A:
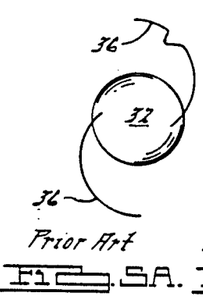
FIGS. 5A and 5B are enlarged views of a common type of intraocular lens.
Figure 5B:
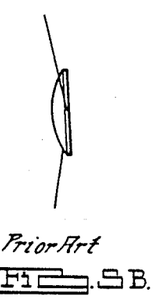

The IOL 32 restores much of the visual acuity of the eye, but has the characteristic of properly focusing only images of objects 34 in FIG. 4 which are within the depth of field 39 of the focusing system, said system being comprised of the IOL 32 and the cornea 13. Other objects, such as the object 41 located in the far field 43, are not in focus, and thus appear blurred. It is also possible, instead, for the focusing system to properly focus objects n the far field 43 but not in the near field 39. The accommodation necessary to selectively focus on both near and far objects, formerly provided by the crystalline lens 19, has thus been reduced or lost.

It is therefore highly desirable to restore accommodation in order to allow the patient with an IOL to selectively focus objects located at all distances. Thus one of the primary objects of the present invention is to provide an improved intraocular lens that can focus objects located at different distances upon the retina, depending upon the relaxed or contracted state of the ciliary body muscles.

One form of the invention comprises a replacement lens for the human eye, which changes in focal length as the ciliary muscle contracts and relaxes.

According to the present invention, an accommodating intraocular lens apparatus includes a lens member having a flexible portion and a relatively rigid portion, with a chamber therebetween. The apparatus also includes an accommodation provision for changing the shape or position of the flexible lens member in response to muscle movement of the eye. Such accommodation feature provides the mechanism to change the refractive characteristics of the flexible lens member and thus allows the intraocular lens patient to focus on objects at varying distances much in the same way as did the patient's natural crystalline lens. In the preferred embodiments, such accommodation capability is provided by way of a hydraulic or other fluid system incorporated into the intraocular lens apparatus for selectively pressurizing and de-pressurizing a fluid-filled (liquid or gaseous) chamber defined by the flexible lens member and a relatively rigid supporting member in order to selectively vary the refractive powers or characteristics of the overall lens system.

Additional objects, advantages and features of the present invention will become apparent from the following description and appended claims taken in conjunction with the accompanying drawings.

BRIEF DESCRIPTION OF THE DRAWINGS

FIG. 23 is a partial cross-sectional view similar to that of FIG. 22, but illustrating an alternate construction.

DETAILED DESCRIPTION OF THE PREFERRED EMBODIMENTS OF THE INVENTION

FIGS. 6 through 24 depict exemplary embodiments of the present invention for purposes of illustration. One skilled in the art will readily recognize from the following description and the accompanying drawings that the principles of the present invention are also applicable to intraocular lenses other than those depicted in the drawings.

Figure 6:
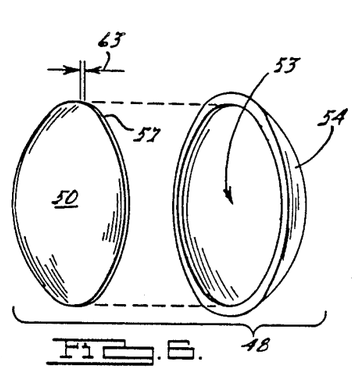
FIG. 6 illustrates an exploded view of an intraocular lens apparatus according to one form of the invention.
Figure 7:
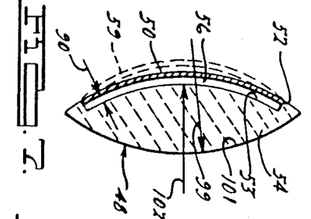
FIG. 7 illustrates a detailed view of the intraocular lens apparatus of FIG. 6 shown in cross-section.

FIG. 6 illustrates one exemplary form of the invention, in which an IOL 48 is shown in cross-section in FIG. 7. A thin, membrane-like lens 50 is sealed along its periphery 52 to a thicker support lens 54, which contains a circular recessed cavity 53, thereby forming a fluid-filled (liquid or gaseous) cavity or chamber 56 (shown in FIG. 7) between the two lenses. Fluid pressure is applied to the chamber 56, by an apparatus discussed below, in order to drive the membrane-lens 50 into the shape or position 59 (shown in phantom lines in FIG. 7). This change in position or shape changes the refractive powers or characteristics of the overall lens system 48, which includes the two lenses 50 and 54 and the fluid chamber 56.

Figures 8A, 8B:
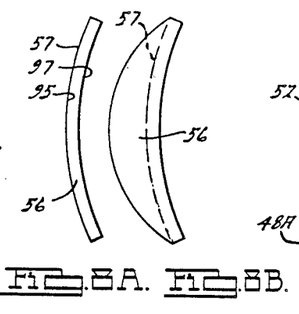
FIGS. 8A and 8B illustrate the change in shape of the chamber of the lens apparatus shown in FIG. 7, which occurs during use of the invention.

The above-mentioned change in refractive characteristics is caused primarily by the change in shape of the chamber 56 from the shape shown in FIG. 8A to that shown in FIG. 8B. Since the chamber 56 is fluid-filled, as is discussed below, it too acts as a lens, and the altered shape shown in FIG. 8B provides a refraction that is different from that of the former shape shown in FIG. 8A. The fluid-filled chamber 56 thus effectively functions as a lens of a variable focal length, making the overall lens 48 have a variable focal length.

Figure 9:
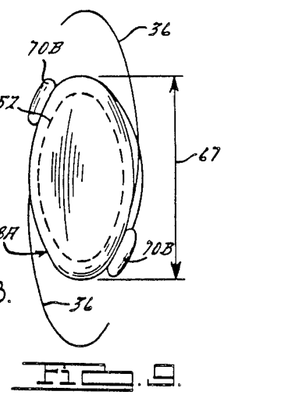
FIG. 9 illustrates one form of the intraocular lens apparatus of the present invention.

In one form of the invention, the IOL 48 of FIG. 6 can be implanted using standard haptics 36, such as those shown in FIG. 9, with the dashed circle 52 indicating the periphery of the membrane lens 50 in FIG. 6. Alternately, a number of supporting bladders 70A are preferably used to lodge the IOL 48 within the capsular bag 20, as shown in FIGS. 10 through 13, and as described in more detail below. The supporting bladders 70A allow an IOL of fixed size, having a given diameter 67, such as that shown in FIG. 9, to be used in eyes having any of several diameters 25 of the capsular bag equator as shown in FIG. 2. Thus the invention is adaptable to patients having capsular bags of different sizes.

Figure 10:
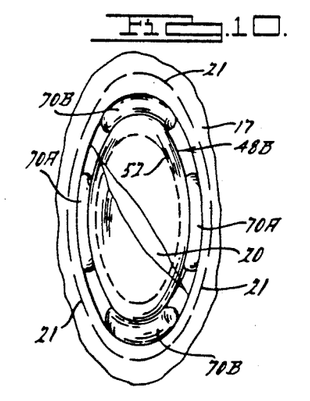
FIG. 10 illustrates another form of the intraocular lens apparatus of the present invention implanted within the ciliary body of the eye.
Figure 11:
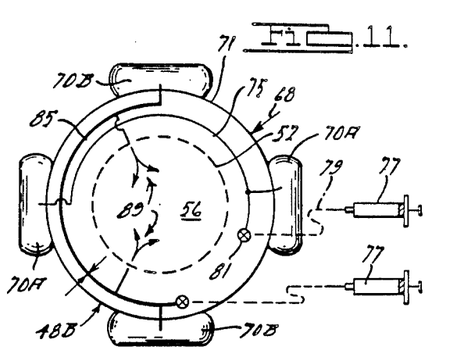
FIG. 11 illustrates a preferred form of the present invention, including pressure sources used to inflate flexible bladders, which contact or expand in response to action of the ciliary body.
Figures 12, 13:
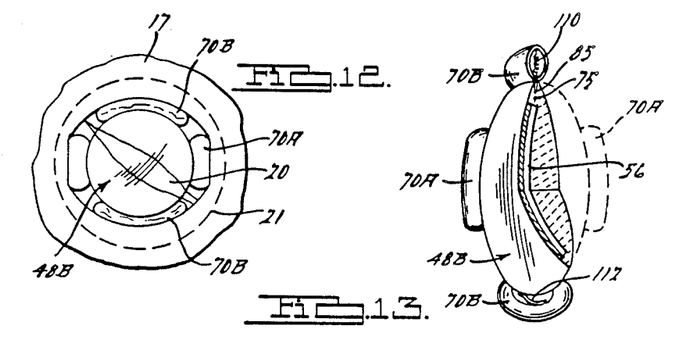
FIG. 12 shows in schematic form how the ciliary body compresses one pair of the bladders shown in FIG. 11.
FIG. 13 shows the apparatus of FIG. 11 in perspective, cut-away form.
Figures 14, 15:
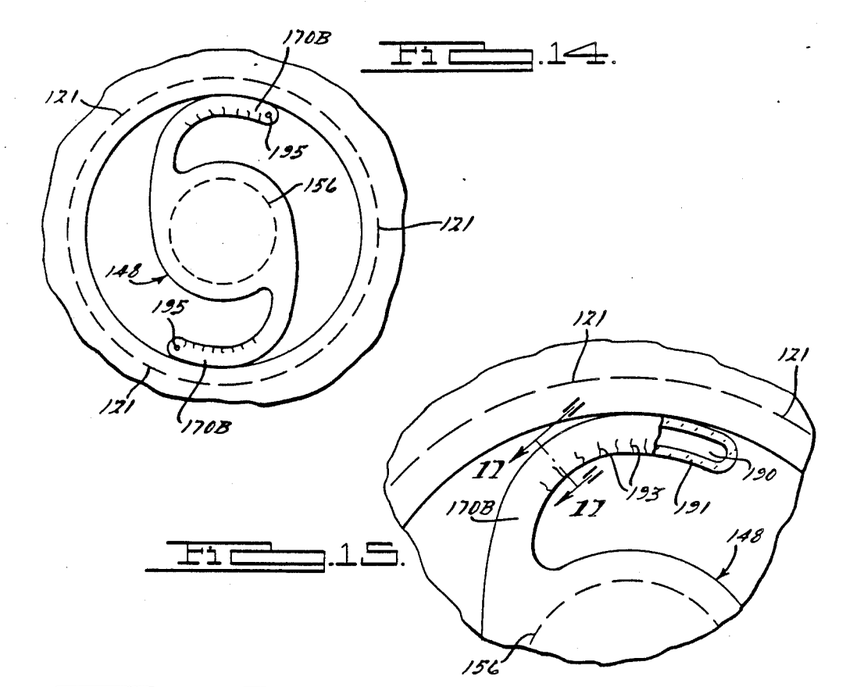
FIG. 14 is a view similar to that of FIG. 10, but illustrating still another form of the intraocular lens apparatus of the present invention.
FIG. 15 is a partial detail view of the lens apparatus of FIG. 14, illustrating a hollow haptic member.
Figure 16:
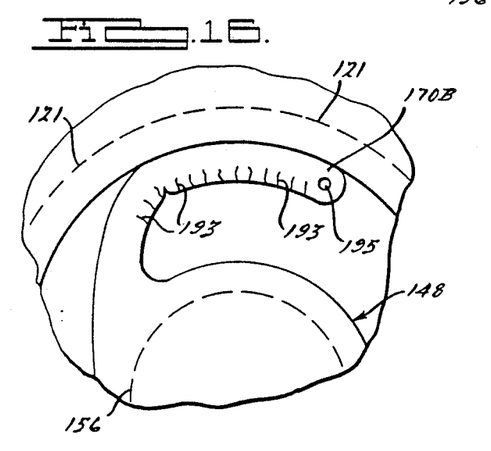
FIG. 16 is a view similar to that of FIG. 15, but illustrating how the ciliary body deforms the hollow haptic member to cause accommodation.
Figure 17:
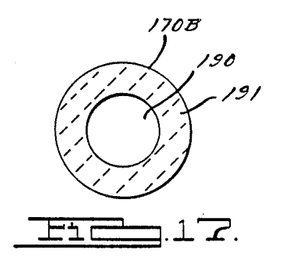
FIG. 17 is a cross-sectional view taken generally along line 17—17 of FIG. 15.

As is shown diagrammatically in FIGS. 11 and 13, the supporting bladders 70A are all connected to a common manifold 75, called a support manifold, which distributes fluid pressure to the bladders 70A. During implantation in the eye, the fluid pressure is applied by a source, such as a syringe 77, through a line 79, which is then removed from a valve 81 when the proper pressure is attained. The bladders 70A are inflated and pressurized until they contact the ciliary body 17, as shown in FIG. 10, at which time the external pressure source 77 is removed.

In either of the exemplary IOL's 48A or 48B, a number of bladders 70B shown in FIGS. 9 through 11, which are termed focusing or accommodation bladders, are all connected to a second, accommodation manifold 85, which is illustrated by a thicker line in order to distinguish it from the support manifold 75. In addition, the accommodation manifold 85 connects in fluid communication with the fluid chamber 56, as indicated by fluid arrows 89. During implantation into the eye, the accommodation bladders 70B are inflated by an external pressure source 77 as described above, but to a lower final pressure than that of the support bladders 70A.

The membrane lens 50 in FIGS. 9 and 10 functions much like a wall of a pressure vessel, which is defined by the chamber 56 and which is in fluid communication with the accommodation manifold 85 and the accommodation bladders 70B. The membrane 50 is a flexible member in tension and supported only at its circular periphery 52, and thus can resist only small internal pressures within the chamber 56 without deformation. Since the flexible membrane 50 has a very low moment of inertia, it deforms into the position 59 in FIG. 7 under a slight increase in fluid pressure.

When focusing, the eye deforms either the IOL of the present invention or the natural crystalline lens 19 in FIG. 1 in similar ways. When the IOL 48A or 48B of the present invention is implanted, the ciliary body 17 contracts, and the focusing bladders 70B became compressed as shown in FIG. 12. This compression forces fluid into the chamber 56 as indicated by fluid arrows 89 in FIG. 11. The membrane lens 50 is thus slightly pressurized and deforms into the shape or position 59 shown in phantom lines in FIG. 7 as the chamber 56 deforms into the shape indicated in FIG. 8B. As discussed above, this deformation allows the lens system to focus nearby objects onto the retina.

Relaxation of the ciliary body 17 operates in reverse, allowing the membrane lens 50 to return to its former position shown in solid lines in FIG. 7, and allowing the excess fluid to flow out of the chamber 56 back to the bladders 70B. Similarly, the chamber 56 adopts its original shape as shown in FIG. 8A, which is proper for focusing distant objects.

It is important to note that the accommodation or focusing IOL 48A or 48B of the present invention functions only when enclosed by the capsular bag 20 in order to restrain the lens in its proper position. Since cataracts can be removed while leaving the capsular bag intact (extracapsular cataract) extraction), the IOL 48A or 48B can be inserted into the capsular bag during implantation. This allows the ciliary body muscles to relax, increasing the aperture diameter and putting the suspensory ligaments or zonules into tension, which in turn tends to flatten the capsular bag and enhance the capability of the IOL to change its shape and refractive characteristics.

It should be noted that the drawings show the invention in exaggerated form for ease of illustration and are not drawn to scale. For example, the diameter 67 in FIG. 9 is preferably about 7.5 mm, while the thickness of the membrane lens 50 in FIG. 6 (i.e., dimension 63) is preferably less than 0.5 mm. Thus, a much larger difference in size exists than the drawings appear to show. Furthermore, the distance 68 in FIG. 11 between the periphery 52 of the membrane lens 50 and the outer edge 71 of the lens body 54 is preferably approximately 1.5 mm, but appears to be greater in FIG. 11, because the diameter of the membrane lens 50 is preferably approximately 6.0 mm.

The chamber 56 is shown in FIG. 7 as having a finite thickness, indicated by dimension 90, with a suitable thickness being approximately 0.1 mm. However, it may be desirable to reduce the thickness to practically zero, in which case the membrane lens 50 would contact the base lens 54 when pressure within the chamber 56 was absent. In this instance, the membrane lens 50 would be separated from the base lens 54 by only a thin layer of fluid wetting the chamber surfaces 95 and 97 shown in FIG. 8A. In either case, it is preferred that the surfaces 95 and 97 have the same radius of curvature and thus that the thickness 90 is substantially uniform.

The lens body 54 is preferably constructed of polymethylethacylate (PMMA), the membrane lens 50 and both bladders 70A and 70B are preferably constructed of a silicone elastomer, and the fluid contained within the bladders and manifolds is preferably a silicone oil. The diameters of the manifolds and channels in FIG. 11 are preferably approximately 0.25 mm. The radius 99 of curvature of the surface 101 in FIG. 7 is preferably approximately 16 mm, and the radius 102 of curvature of the membrane lens 50 is preferably in the range of approximately 11 mm to 16 mm, depending upon the fluid pressure applied.

Two support bladders 70A and two focusing bladders 70B are shown in FIG. 11. However, different numbers of each bladder type can be used in accordance with the invention. It is expected that satisfactory performance in accordance with the present invention can be secured with one, two, three, four, or even more support and/or accommodation bladders on the IOL. However, it is also possible to support the IOL without the support bladders 70A, but rather with conventional haptics 36, as shown in FIG. 9 and discussed above.

It is possible in some circumstances, that viscous fluid forces within the manifold 85 shown in FIG. 11 can retard fluid flow and increase the time needed to fill and empty the chamber 56. Consequently, it may be desirable to spring-bias the accommodation or focusing bladders 70B by springs (as shown in FIG. 13). Thus, when the pressure from the ciliary body 17 is relaxed, the springs act to expand the focusing bladder 70B, thus applying a negative pressure to the chamber 56. This negative pressure assists in overcoming the viscous fluid forces. These springs can be the coil springs 110, or the optional leaf springs 112 attached to the lens body 54, or other known types of resilient biasing devices.

It is preferred that the lens body 54 in FIG. 7 is positioned posterior to the membrane lens 50 in the event that a phenomenon called posterior capsule opacification occurs. In this event, the posterior surface of the capsular bag 20, which formerly contained the crystalline lens 19 and which, after implantation, contains an IOL becomes cloudy or opaque. A typical treatment for this condition is to remove part of the capsule, or to rupture it, using an Yttrium-Aluminum-Garnet (YAG) laser. However, the proximity of the posterior of the capsular bag to the posterior of the IOL possibly could result in the laser damaging the IOL. In the present invention, however, the lens base 54 is quite thick and thus more resistant to such damage than is the membrane lens 50.

The diameter of the membrane lens 50 should be approximately 6.0 mm, which generally is sufficient to occupy the fully dilated human iris. In this way, the pupil does not expose any of the apparatus in FIG. 11, which is positioned radially outward of the periphery 52.

In order to protect against the possibility of failure of the accommodating IOL 48A or 48B, the lens is designed such that when the membrane lens 50 in FIG. 7 is fully relaxed, the refractive characteristics of the lens system 48A or 48B allow the patient to view objects in a range of infinity to 6 feet (depending on pupil size and overall refractive error in the patient's eye). In this way, reduced, but acceptable, vision is still available to the patient without, or prior to, replacement of a failed lens.

FIGS. 14 through 24 illustrate further alternate embodiments of an intraocular lens apparatus according to the present invention. Many of the elements of the embodiments depicted in FIGS. 14 through 24 are generally similar, at least in terms of their function, to corresponding elements of the embodiments shown in FIGS. 6 through 13. Therefore, similar reference numerals have been used in FIGS. 14 through 24 to indicate such corresponding elements, except that the reference numerals in FIGS. 14 through 24 have either one-hundred or two-hundred prefixes.

FIGS. 14 through 19 depict various versions of an alternate embodiment of the invention, wherein IOL 148 is substantially identical to the lens apparatus shown in FIGS. 6 through 13, except that the accommodation bladders 70B and the support bladders 70A are replaced by one or more accommodating haptic members 170B. The accommodating haptic members 170B are constructed in the form of a generally hollow, elongated, tubular-shaped haptic member containing fluid and attached to the outer periphery of the IOL 148 in fluid communication with the fluid chamber 156.

Figure 18:
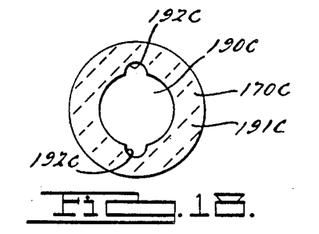
FIG. 18 is a cross-sectional view similar to that of FIG. 17, but illustrating an alternate haptic construction.
Figures 19, 20:
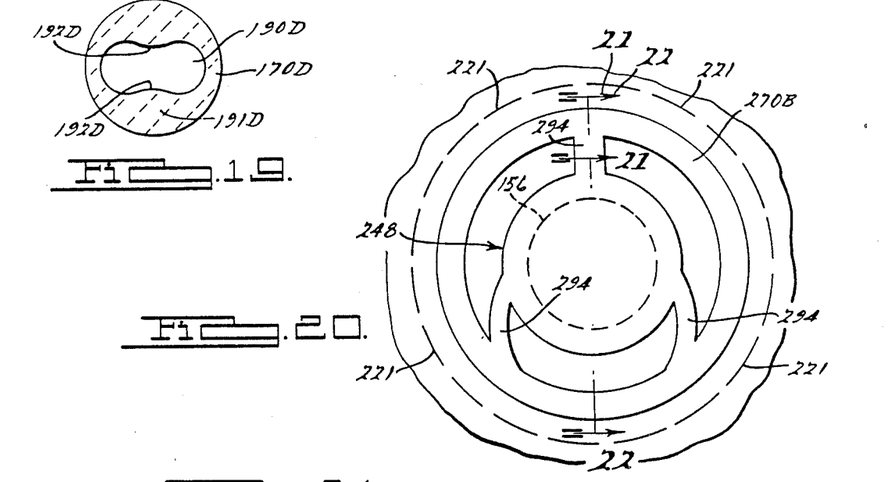
FIG. 19 is a cross-sectional view similar to that of FIGS. 17 and 18, but illustrating still another alternate haptic construction.
FIG. 20 is a view similar to that of FIGS. 10 and 14, but diagrammatically illustrate still another form of the present invention.

When focusing, the muscle fibers 121 of the ciliary body contract and expand in order to forcibly deform or relax the hollow accommodating haptic members 170B, thereby forcing fluid into, or withdrawing fluid from, the chamber 156 in a manner similar to that described above in connection with FIGS. 9 through 13. In this way, the accommodation feature of the present invention can be advantageously combined with the supporting function of the haptic members 36 or the supporting bladders 70A described above. When the muscle fibers 121 of the ciliary body contract in a manner diagrammatically illustrated in FIG. 16, the hollow accommodating haptic members 170B are compressed and may even deform into the kinked configuration shown for purposes of illustration in FIG. 16. Thus, it may be found to be desirable to guard against the hollow accommodating haptic member 170B collapsing and closing off the interior chamber 190, which could cause undesirably high fluid pressures in the interior chamber 190 or the fluid-filled chamber 156 of the lens portion of the apparatus. Thus, it may be desirable to form the interior chamber 190 in a non-circular or noncylindrical shape. Two examples of such non-circular cross-sectional shape are illustrated in FIGS. 18 and 19, wherein the thickness of the haptic wall 191C and 191D, respectively, is non-uniform about the hollow haptic members 170C and 170D, respectively. Such non-uniform wall thickness is created by the provision of internal discontinuities 192C and 192D, respectively, which serve to substantially prevent total closing off of the fluid flow paths in the event of collapse of all or a portion of the hollow haptic member during ciliary contraction.

In addition, since the compression, deformation or kinking of the hollow haptic members 170B must be capable of being accomplished merely by the force of ciliary muscle contraction, it also may be desirable to provide ribs or other discontinuities 193 on the external periphery of the hollow accommodating haptic members 170B. Also, a suitable means for introducing fluid into the hollow haptic members 170B and thus the fluid-filled chamber 156B should also be provided, such as the fill port 195 shown for purposes of illustration in FIGS. 14 and 16.

FIGS. 20 through 24 illustrate still another embodiment of the present invention, wherein the IOL 248 is equipped with a fluid-filled hollow ring or conduit 270B surrounding the lens portion of the IOL 248. The circular conduit 270B functions in a manner generally similar to that described above in connection with FIGS. 14 through 19, and has its interior chamber 290 in fluid communication with the fluid-filled chamber 256 by way of one or more interconnecting hollow ducts 294.

Figures 21, 22:
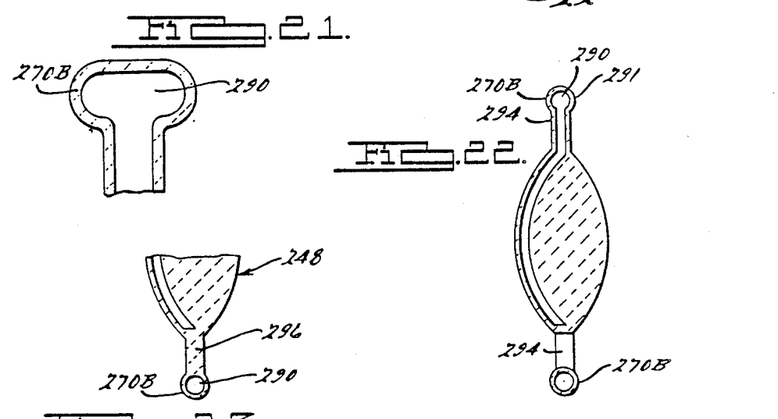
FIG. 21 is a partial cross-sectional view taken generally along line 21—21 of FIG. 20.
FIG. 22 is a cross-sectional view taken generally along line 22—22 of FIG. 20.

As shown in FIG. 21, the contraction of the muscle fibers (shown diagrammatically at reference numeral 221) causes an inwardly-directed force on the conduit 270B. This force compresses or deforms the conduit 270B to force fluid from the conduit 270B, through the interconnecting ducts 294, and into the fluid-filled chamber 256. When the muscle fibers 221 relax, the conduit 270B returns to its relatively relaxed and undeformed condition, thereby allowing the fluid pressure in the fluid-filled chamber 256 to be relieved, similar to the function described above in connection with the previously-mentioned embodiments of the present invention. Also, like the hollow accommodating haptic members 170B shown in FIGS. 14 through 19, the conduit 270B also serves the function of supporting the IOL 248 in the eye, and thus acts as a haptic member.

Although the interconnecting ducts 294 are shown as extending in generally radial directions and interconnected with the lens portion of the IOL 248 in a generally straight-on relationship therewith, it may be found to be desirable to form the ducts 294 in a "swept" or arcuate configuration, having a more "tangential" interconnection with the lens portion of the IOL 248, similar to that shown for purposes of illustration in FIG. 22.

Figure 24:
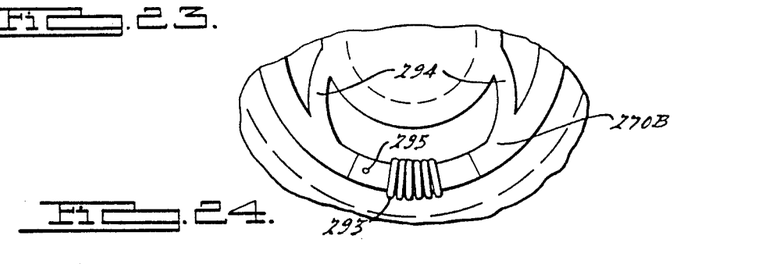
FIG. 24 is a partial detailed view of the apparatus of FIG. 20, but illustrating an optional construction.

Also, as was mentioned above in connection with the embodiment depicted in FIGS. 14 through 19, the conduit 270B can be desirably equipped with ribs or other discontinuities 293 in order to facilitate the proper compression and expansion in response to ciliary body muscle movement. In this regard, it should be noted that at least a portion of the ribs or other discontinuities 293 can be in the form of a circumferentially collapsable and expandable portion of the conduit 270B, as shown in FIG. 24. Such an arrangement allows the circumference of the conduit 270B to be adjustably increased or decreased in order to fit a variety of eye sizes. This is especially advantageous since the conduit 270B also serves the above-mentioned haptic function of holding and supporting the IOL 248 in the eye.

Finally, as illustrated in FIG. 23, one or more interconnecting members 296, which need not be hollow, can be provided to support the conduit 270B in its spaced-apart relationship with the lens portion of the IOL 248. Such non-hollow interconnecting members 296 (if included) function merely to aid in maintaining the lens portion of the IOL 248 in its proper position after implantation in the eye.

The foregoing discussion discloses and describes exemplary embodiments of the present invention. One skilled in the art will readily recognize from such discussion, and from the accompanying drawings and claims, that various changes, modifications and variations can be made therein without departing from the spirit and scope of the invention as defined in the following claims.

We claim:

1. An intraocular apparatus for implantation in an eye, said apparatus comprising:

a lens assembly including inner and outer light-transmissive lens members defining a fluid-filled chamber located between said lens members, at least a portion of said outer lens member being flexible; and accommodation means for changing the shape of said chamber in response to muscle movement in the eye in order to change the overall refractive characteristics of said lens assembly, said accommodation means including fluid means for selectively changing the fluid pressure in said fluid-filled chamber in order to change the position of said outer lens member relative to said inner lens member.

2. An intraocular apparatus according to claim 1, wherein said fluid means includes a flexible fluid-filled bladder, said chamber being in fluid communication with said fluid-filled chamber, said bladder being sized for contact with muscles in the eye and being contractable and expandable in response to said eye muscle movement in order to respectively force fluid into, and withdraw fluid out of, said chamber in order to cause a change in the position of said outer lens member relative to said inner lens member in response to said eye muscle movement.

3. An intraocular lens apparatus adapted to be implanted in the eye, said apparatus comprising:

a transparent and flexible outer lens membrane;

a transparent and relatively rigid inner support lens member located adjacent said flexible membrane, said flexible lens membrane and said support lens member being spaced apart and sealed to one another and defining a fluid chamber therebetween; and accommodation means for injecting a pressurized fluid into said fluid chamber between said outer lens membrane and said inner support lens member in response to eye muscle movement in order to resiliently deform said flexible outer lens membrane and thereby change the refractive characteristic of said intraocular lens apparatus.

4. An intraocular lens apparatus according to claim 3, wherein said accommodation means includes at least one fluid-filled inflatable accommodation bladder in fluid communication with said fluid chamber, said accommodation bladder being selectively contractable and expandable in response to eye muscle movement in order to selectively inject and withdraw said pressurized fluid into and out of said fluid chamber.

5. An intraocular lens apparatus according to claim 4, wherein said apparatus further comprises at least one flexible fluid-filled support bladder, said support bladder being disposed on the outer periphery of said inner support lens member and sized for contacting the ciliary body of the eye in order to support said intraocular lens apparatus in the eye.

6. An intraocular lens apparatus according to claim 5, wherein said intraocular lens apparatus is adapted for implantation in the capsular bag of the eye.

7. An intraocular lens apparatus according to claim 5, wherein said accommodation bladder and said support bladder are separate bladders.

8. An intraocular lens apparatus according to claim 5, wherein said accommodation bladder and said support bladder are the same bladder.

9. An intraocular lens apparatus according to claim 4, wherein said apparatus further comprises at least one haptic member, said haptic member being disposed on the outer periphery of said inner support lens member and sized for contacting the ciliary body of the eye in order to support said intraocular lens apparatus in the eye.

10. An intraocular lens apparatus according to claim 9, wherein said intraocular lens apparatus is adapted for implantation in the capsular bag of the eye.

11. An intraocular lens apparatus according to claim 4, wherein said apparatus further includes resilient biasing means for resiliently biasing said accommodation bladder toward its expanded condition.

12. An intraocular lens apparatus according to claim 11, wherein said resilient biasing means includes a spring disposed within said accommodation bladder.

13. An intraocular lens apparatus according to claim 11, wherein said resilient biasing means includes a spring disposed between a portion of said support lens and said accommodation bladder.

14. An intraocular apparatus for implantation in an eye, said apparatus comprising:
a lens assembly including inner and outer light-transmissive lens members defining a fluid-filled chamber located between said lens members, at least a portion of said outer lens member being flexible; and
accommodation means for changing the shape of said chamber in response to muscle movement in the eye in order to change the overall refractive characteristics of said lens assembly, said accommodation means including fluid means for selectively changing the fluid pressure in said fluid-filled chamber in order to change the position of said outer lens member relative to said inner lens member, said fluid means further including at least one elongated hollow and generally tubular-shaped haptic member interconnected with said inner and outer lens members, said hollow haptic member including external peripheral surface thereon and an interior wall defining an interior volume, said interior volume having said fluid therein and being in fluid communication with said fluid-filled chamber, at least a portion of said hollow haptic member being contractable and expandable in response to said eye muscle movement in order to respectively force fluid into, and withdraw fluid out of, said fluid-filled chamber in order to cause a change in the position of said outer lens member relative to said inner lens member in response to said eye muscle movement.

15. An intraocular lens apparatus according to claim 14, wherein said hollow haptic member has external discontinuities on said external peripheral surface, said discontinuities tending to facilitate said contraction and expansion in response to said eye muscle movement.

16. An intraocular lens apparatus according to claim 15, wherein said discontinuities include ribs extending around at least a portion of said external peripheral surface.

17. An intraocular lens apparatus according to claim 14, wherein said hollow haptic member has a non-circular hollow internal cross-sectional shape in order to substantially prevent complete collapse of said hollow haptic member during said contraction.

18. An intraocular lens apparatus according to claim 17, wherein said hollow haptic member has external discontinuities on said external peripheral surface, said discontinuities tending to facilitate said contraction and expansion in response to said eye muscle movement.

19. An intraocular lens apparatus according to claim 18, wherein said discontinuities include ribs extending around at least a portion of said external peripheral surface.

20. An intraocular lens apparatus according to claim 17, wherein said internal cross-sectional shape of said hollow haptic member includes at least one inwardly-protruding portion of said interior wall.

21. An intraocular lens according to claim 17, wherein the lateral distance between said external peripheral surface and said interior wall being non-uniform around said hollow haptic member.

22. An intraocular apparatus for implantation in an eye, said apparatus comprising:
a lens assembly including inner and outer light-transmissive lens members defining a fluid-filled chamber located between said lens members, at least a portion of said outer lens member being flexible; and
accommodation means for changing the shape of said chamber in response to muscle movement in the eye in order to change the overall refractive characteristics of said lens assembly, said accommodation means including fluid means for selectively changing the fluid pressure in said fluid-filled chamber in order to change the position of said outer lens member relative to said inner lens member, said fluid means further including an elongated generally circular hollow conduit extending circumferentially around the periphery of said inner and outer lens members, said hollow conduit including an external peripheral surface thereon and an interior wall defining an interior volume of said hollow conduit, said interior volume having said fluid therein and being in fluid communication with said fluid-filled chamber, at least a portion of said hollow conduit being contractable and expandable in order to respectively force fluid into, and withdraw fluid out of, said fluid-filled chamber in order to cause a change in the position of said outer lens member relative to said inner lens member in response to said eye muscle movement.

23. An intraocular lens apparatus according to claim 22, wherein said hollow conduit has external discontinuities on said external peripheral surface, said discontinuities tending to facilitate said contraction and expansion in response to said eye muscle movement.

24. An intraocular lens apparatus according to claim 23, wherein said discontinuities include ribs extending around at least a portion of said external peripheral surface.

25. An intraocular lens apparatus according to claim 22, wherein at least a portion of said hollow conduit is spaced apart from said periphery of said inner and outer lens members, said interior volume being interconnected with said fluid-filled chamber by one or more interconnecting hollow ducts extending between said hollow conduit and said inner and outer lens members.

26. An intraocular lens apparatus according to claim 25, wherein said hollow duct extends generally radially between said hollow conduit and said inner and outer lens members.

27. An intraocular lens apparatus according to claim 25, wherein said hollow duct extends along a generally arcuate path between said hollow conduit and said inner and outer lens members.

28. An intraocular lens apparatus according to claim 25, wherein a portion of said hollow conduit is selectively expandable and contractable circumferentially at least prior to said implantation in the eye in order to allow said apparatus to be sized to fit a number of different eye sizes.

* * * * *

UNITED STATES PATENT AND TRADEMARK OFFICE
CERTIFICATE OF CORRECTION

PATENT NO. : 4,932,966

DATED : June 12, 1990

INVENTOR(S) : Bruce A. Christie, et al

It is certified that error appears in the above-identified patent and that said Letters Patent is hereby corrected as shown below:

Column 3, line 63, "48" should be --48B--

Column 4, line 42, "became" should be --become--

Column 10, line 29, claim 20, "of" should be --on--

Signed and Sealed this

Twenty-fourth Day of September, 1991

*Attest:*

HARRY F. MANBECK, JR.

*Attesting Officer*      *Commissioner of Patents and Trademarks*